(12) United States Patent
Ino et al.

(10) Patent No.: US 9,309,486 B2
(45) Date of Patent: *Apr. 12, 2016

(54) CLEANING AGENT COMPOSITION

(71) Applicant: AJINOMOTO CO., INC., Chuo-ku (JP)

(72) Inventors: Masahiro Ino, Kawasaki (JP); Naoaki Ikeda, Kawasaki (JP); Takanori Sugimoto, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 100 days.

This patent is subject to a terminal disclaimer.

(21) Appl. No.: 14/064,659

(22) Filed: Oct. 28, 2013

(65) Prior Publication Data

US 2014/0051772 A1      Feb. 20, 2014

Related U.S. Application Data

(63) Continuation of application No. PCT/JP2012/061430, filed on Apr. 27, 2012.

(30) Foreign Application Priority Data

Apr. 28, 2011    (JP) ................. 2011-102500

(51) Int. Cl.
| | | |
|---|---|---|
| C11D 3/33 | (2006.01) |
| A61Q 5/02 | (2006.01) |
| A61Q 19/10 | (2006.01) |
| A61K 8/44 | (2006.01) |
| A61K 8/42 | (2006.01) |
| C11D 3/32 | (2006.01) |

(52) U.S. Cl.
CPC ... *C11D 3/33* (2013.01); *A61K 8/42* (2013.01); *A61K 8/44* (2013.01); *A61Q 5/02* (2013.01); *A61Q 19/10* (2013.01); *C11D 3/32* (2013.01)

(58) Field of Classification Search
CPC ........... A61K 8/42; A61K 8/44; A61Q 19/10; A61Q 5/02; C11D 3/32; C11D 3/33
See application file for complete search history.

(56) References Cited

U.S. PATENT DOCUMENTS

| | | | | |
|---|---|---|---|---|
| 5,147,868 A | * | 9/1992 | Graham et al. | ................ 514/119 |
| 5,234,909 A | * | 8/1993 | Philippe | ........................ 514/18.8 |
| 5,529,712 A | * | 6/1996 | Sano et al. | ..................... 510/481 |

FOREIGN PATENT DOCUMENTS

| | | |
|---|---|---|
| EP | 1 672 055 A1 | 6/2006 |
| JP | 55-40669 A | 3/1980 |
| JP | 2005-325188 A | 11/2005 |
| JP | 2005325188 A * | 11/2005 |
| WO | WO 94/22994 A1 | 10/1994 |

OTHER PUBLICATIONS

Extended European Search Report issued Sep. 18, 2014, in European Patent Application No. 12777189.7.
U.S. Appl. No. 14/064,454, filed Oct. 28, 2013, Ino, et al.
International Search Report issued Jul. 31, 2012 in PCT/JP2012/061430.

* cited by examiner

*Primary Examiner* — Sean Basquill
*Assistant Examiner* — Mark V Stevens
(74) *Attorney, Agent, or Firm* — Oblon, McClelland, Maier & Neustadt, L.L.P.

(57) ABSTRACT

The problem of the present invention is provision of a cleansing composition providing good amount and good quality of lather. Using a particular alkenoic acid or a salt thereof, the above-mentioned problem can be solved. In addition, the cleansing composition provided by the present invention is stable in various formulations and also useful for rough skin and damaged hair.

19 Claims, No Drawings

CLEANING AGENT COMPOSITION

TECHNICAL FIELD

The present invention relates to a cleansing composition containing a particular alkenoic acid or a salt thereof.

BACKGROUND ART

While anionic surfactants are widely used for cleansing compositions and show superior detergency, they are not satisfactory since the amount of lather is not necessarily sufficient, the lather quality is rough and the lather is easily broken. In addition, anionic surfactants are not necessarily satisfactory for use for rough skin and damaged hair, and a particular system sometimes instabilizes the quality of the cleansing composition.

SUMMARY OF THE INVENTION

Problems to be Solved by the Invention

It is an object of the present invention to provide a novel cleansing composition providing a good amount of lather and good lather quality.

Means of Solving the Problems

The present inventors have conducted intensive studies in view of the above-mentioned problems, and found that the above-mentioned problems can be solved by using a particular alkenoic acid or a salt thereof, and further that the obtained cleansing composition is stable in various formulations and useful for rough skin and damaged hair.

Accordingly, the present invention includes the following embodiments.

[1] A cleansing composition comprising
(Component A) a compound represented by the formula (1):

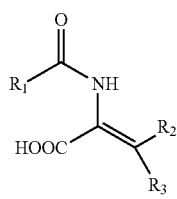

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6 carbon atoms, preferably 1 to 5 carbon atoms, or a salt thereof.

[2] The cleansing composition of [1], wherein $R_1$ is a saturated or unsaturated, linear or branched-chain hydrocarbon group having 9 to 13 carbon atoms.

[3] The cleansing composition of [1] or [2], wherein one of $R_2$ and $R_3$ is a methyl group, and the other is a hydrogen atom.

[4] The cleansing composition of [1], wherein (Component A) is 2-dodecanamido-2-butenoic acid or a salt thereof.

[5] The cleansing composition of any of [1]-[4], further comprising (Component B) fatty acid or a salt thereof.

[6] The cleansing composition of [5], wherein (Component B) is lauric acid or a salt thereof.

[7] The cleansing composition of any of [1]-[6], further comprising (Component C) a compound represented by the formula (2):

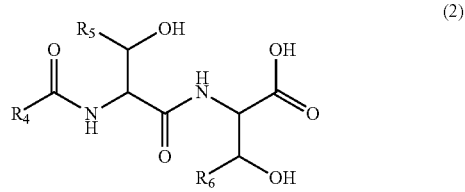

wherein $R_4$ is a saturated or unsaturated, linear or branched-chain hydrocarbon group having 7 to 25 carbon atoms, and $R_5$ and $R_6$ are each independently a hydrogen atom or an alkyl group having 1 to 6 carbon atoms, preferably 1 to 5 carbon atoms, or a salt thereof.

[8] The cleansing composition of [7], wherein $R_4$ is a saturated or unsaturated, linear or branched-chain hydrocarbon group having 9 to 13 carbon atoms.

[9] The cleansing composition of [7] or [8], wherein $R_5$ and $R_6$ are each a methyl group.

[10] The cleansing composition of [7], wherein (Component C) is 2-(2-dodecanoylamino-3-hydroxybutanoylamino)-3-hydroxybutanoic acid or a salt thereof.

[11] A cosmetic agent comprising the cleansing composition of any of [1]-[10].

[12] Use of a compound represented by the formula (1):

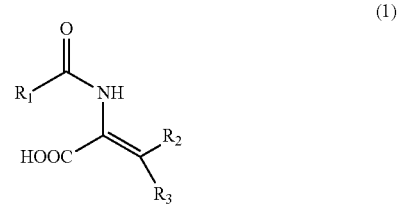

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6 carbon atoms, or a salt thereof for producing a cleansing composition.

[13] Use of a compound represented by the formula (1):

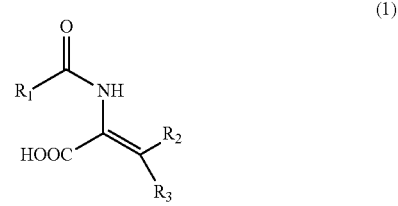

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6 carbon atoms, or a salt thereof for increasing the amount of lather and/or improving the lather quality of a cleansing composition.

[14] Use of a compound represented by the formula (1):

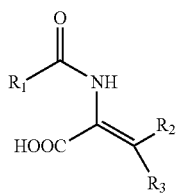

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6 carbon atoms, or a salt thereof for stabilizing the quality of a cleansing composition.

[15] Use of a compound represented by the formula (1):

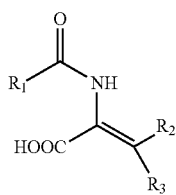

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6 carbon atoms, or a salt thereof for giving moisture (or moist touch) to the skin and/or reducing further damage on the hair.

Effect of the Invention

According to the present invention, a cleansing composition providing a good amount and good quality of lather can be provided by using a particular alkenoic acid or a salt thereof. In addition, the cleansing composition is stable in various formulations, does not easily cause further damage even when used for rough skin and damaged, hair, and can give moisture (or moist touch). Hence, the present invention can provide a cleansing composition satisfactory even for rough skin and damaged hair.

DESCRIPTION OF EMBODIMENTS (Component A)

The present invention is a cleansing composition containing a particular alkenoic acid or a salt thereof (Component A).

The alkenoic acid for component A to be used in the present invention is a compound represented by the formula (1) (hereinafter sometimes to be referred to as "compound (1)").

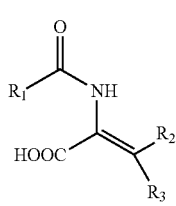

wherein $R_1$ is a saturated or unsaturated, linear or branched-chain hydrocarbon group having 7 to 25 carbon atoms, and $R_2$ and $R_3$ are each independently a hydrogen atom or an alkyl group having 1 to 6, preferably 1 to 5, carbon atoms.

$R_1$ is a saturated or unsaturated, linear or branched-chain hydrocarbon group having 7 to 25 carbon atoms. The carbon number is preferably 7 to 21, more preferably 7 to 15, further preferably 9 to 15, most preferably 9 to 13. The hydrocarbon group is preferably an alkyl group, specifically, a group having 7 to 25 carbon atoms, such as a heptyl group, an octyl group, a nonyl group, a decyl group, an undecyl group, a tridecyl group, a tetradecyl group, a pentadecyl group, a heptadecyl group, an octadecyl group, a nonadecyl group, an icosyl group, an eicosyl group, a henicosyl group, a heneicosyl group, a docosyl group, a tricosyl group, a tetracosyl group, a pentacosyl group, an isoheptyl group, an isooctyl group, an isononyl group, an isodecyl group, an isoundecyl group, an isotridecyl group, an isotetradecyl group, an isopentadecyl group, an isoheptadecyl group, an isooctadecyl group, an isononadecyl group, an isoicosyl group, an isoeicosyl group, an isohenicosyl group, an isoheneicosyl group, an isodocosyl group, an isotricosyl group, an isotetracosyl group, an isopentacosyl group and the like. From the aspect of solubility of component A, a group having 7 to 15 carbon atoms, such as a heptyl group, a nonyl group, an undecyl group, a tridecyl group, a pentadecyl group and the like, is preferable, a group having 9 to 13 carbon atoms, such as a nonyl group, an undecyl group, a tridecyl group and the like, is more preferable, and an undecyl group is most preferable from the aspects of the amount and quality of lather afforded by the obtained cleansing composition.

$R_2$ and $R_3$ are each independently a hydrogen atom or an alkyl group having 1 to 6 carbon atoms. The alkyl group having 1 to 6 carbon atoms may be linear or branched-chain. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1,2-dimethylpropyl group, a 1-ethylpropyl group, a hexyl group, an isohexyl group, a 1,1-dimethylbutyl group, a 2,2-dimethylbutyl group, a 3,3-dimethylbutyl group, a 2-ethylbutyl group, and the like. Among these, an alkyl group having 1 to 5 carbon atoms is preferable, an alkyl group having 1 to 4 carbon atoms is more preferable, an alkyl group having 1 to 3 carbon atoms is further preferable, a methyl group, an ethyl group and a propyl group are particularly preferable, and a methyl group is most preferable. Moreover, from the aspects of the amount and quality of lather, $R_2$ and $R_3$ are each preferably a hydrogen atom or a methyl group, and more preferably, one of $R_2$ and $R_3$ is a methyl group, and the other is a hydrogen atom.

Examples of compound (1) include 2-decanamido-2-butenoic acid, 2-decanamido-2-pentenoic acid, 2-decanamido-2-hexenoic acid, 2-decanamido-2-heptenoic acid, 2-decanamido-2-octenoic acid, 2-dodecanamido-2-butenoic acid, 2-dodecanamido-2-pentenoic acid, 2-dodecanamido-2-hexenoic acid, 2-dodecanamido-2-heptenoic acid, 2-dodecanamido-2-octenoic acid, 2-tetradecanamido-2-butenoic acid, 2-tetradecanamido-2-pentenoic acid, 2-tetradecanamido-2-hexenoic acid, 2-tetradecanamido-2-heptenoic acid, 2-tetradecanamido-2-octenoic acid and the like. Of these, from the aspects of the amount and quality of lather, 2-decanamido-2-butenoic acid, 2-dodecanamido-2-butenoic acid, 2-tetradecanamido-2-butenoic acid and 2-decanamido-2-hexenoic acid are preferable, 2-decanamido-2-butenoic acid, 2-dodecanamido-2-butenoic acid and 2-tetradecanamido-2-butenoic acid are more preferable, and 2-dodecanamido-2-butenoic acid is further preferable.

Component A in the present invention can be a salt of compound (1). While the salt of compound (1) is not particularly limited, for example, alkali metal salt such as sodium salt, potassium salt, lithium salt and the like; alkaline earth metal salt such as calcium salt, magnesium salt and the like; ammonium salt such as alkanol amine salt and the like; basic organic compound salt and the like can be mentioned. From the aspects of good amount and good quality of lather, and high solubility, sodium salt, potassium salt and ammonium salt are preferable, sodium salt and potassium salt are more preferable, and sodium salt is most preferable.

Component A in the present invention can be produced by a known method. For example, component A can be prepared by heating alkylamide and 2-ketoalkanoic acid under reflux in a solvent, and condensing the mixture. Examples of alkylamide include laurylamide, myristylamide, palmitylamide, stearylamide, coconut oil alkylamide and the like. Examples of 2-ketoalkanoic acid include 2-ketobutanoic acid, 2-ketopentanoic acid, 2-ketohexanoic acid and the like. As the solvent, any aprotonic solvent can be used without any particular limitation. For example, toluene, xylene, N,N-dimethylformamide, dimethyl sulfoxide and the like can be mentioned.

The content of component A in the cleansing composition of the present invention is not particularly limited as long as it has detergent property. The content of component A in the cleansing composition is preferably not less than 0.00001 wt %, more preferably not less than 0.0001 wt %, further preferably not less than 0.001 wt %, still more preferably not less than 0.01 wt %, from the aspect of rich amount of lather. In addition, the content of component A in the cleansing composition is preferably not more than 30 wt %, more preferably not more than 27 wt %, further preferably not more than 24 wt %, still more preferably not more than 21 wt %, especially preferably not more than 18 wt %, particularly preferably not more than 15 wt %, from the aspect of superior stability in dissolution state. The "weight" and "mass" in the present specification are treated as synonymous terms, and "wt %" and "parts by weight" are treated as synonymous terms with "mass %" and "parts by mass".

When component A in the present invention is contained in a cleansing composition, it can provide an appropriate viscosity to the cleansing composition. With this property of component A, particularly when the cleansing composition is a liquid, handling property can be improved since the cleansing composition does not easily drip from the palm during use, and an image of high quality can be conferred by providing a rich texture.
(Component B)

When fatty acid or a salt thereof (Component B) is further contained in the cleansing composition of the present invention, the amount of lather can be effectively increased and the quality of lather can be improved.

The fatty acid for component B is not particularly limited as long as the amount of lather increases and the quality of lather is improved, and may be linear or branched-chain, and saturated or unsaturated. While the carbon number of the fatty acid in the present invention is not particularly limited, the carbon number of 8 to 22 is preferable, 8 to 18 is more preferable, and 10 to 14 is further preferable. Specific examples include lauric acid, myristic acid, palmitic acid, stearic acid, coconut oil fatty acid, hydrogenated tallow fatty acid, oleic acid and the like. These fatty acids may be used alone, or two or more kinds thereof may be used in combination. In the present invention, of these, lauric acid, myristic acid, palmitic acid, stearic acid and coconut oil fatty acid are preferable, lauric acid and coconut oil fatty acid are more preferable, and lauric acid is further preferable, since the amount of lather can be increased and the quality of lather can be improved.

Component B in the present invention can be a salt of fatty acid. The salt of fatty acid is not particularly limited as long as the amount of lather increases and the quality of lather is improved. Specific examples include alkali metal salts such as sodium salt, potassium salt and the like; organic amine salts such as monoethanolamine salt, diethanolamine salt, triethanolamine salt, 2-amino-2-methyl-1-propanol salt, 2-amino-2-methyl 1,3-propanediol salt and the like; and basic organic compound salt and the like.

The content of component B in the cleansing composition of the present invention is preferably not less than 0.0001 wt %, more preferably not less than 0.001 wt %, further preferably not less than 0.01 wt %, still more preferably not less than 0.1 wt %, especially preferably not less than 0.3 wt %, particularly preferably 1 wt %, of the cleansing composition, since the amount of lather is rich. The content of component B is preferably not more than 90 wt %, more preferably not more than 50 wt %, further preferably not more than 45 wt %, still more preferably not more than 40 wt %, especially preferably not more than 35 wt %, particularly preferably not more than 30 wt %, of the cleansing composition since the stability in dissolution state is superior.

The weight ratio of component B relative to the total weight of component A and component B (B/(A+B)) in the cleansing composition of the present invention is preferably not less than 0.01, more preferably not less than 0.1, further preferably not less than 0.2, still more preferably not less than 0.3, especially preferably not less than 0.4, particularly preferably not less than 0.5, since the amount and quality of lather can be improved, and the stability in dissolution state can be maintained. The weight ratio of component B relative to the total weight of component A and component B (B/(A+B)) in the cleansing composition of the present invention is preferably not more than 0.99999, more preferably not more than 0.9999, further preferably not more than 0.999, still more preferably not more than 0.995, especially preferably not more than 0.99, particularly preferably not more than 0.98, since the amount and quality of lather can be improved, and the stability in dissolution state can be maintained.
(Component C)

In the cleansing composition of the present invention, further addition of a particular alkanoic acid or a salt thereof (Component C) improves skin slippery touch (smooth touch) after washing, hair slippery touch (dry touch), hair lightness and hair combing property, and a cleansing composition with less slimy touch and sliminess can be provided.

The alkanoic acid for component C to be used in the present invention is preferably a compound represented by the formula (2) (hereinafter sometimes to be referred to as "compound (2)"):

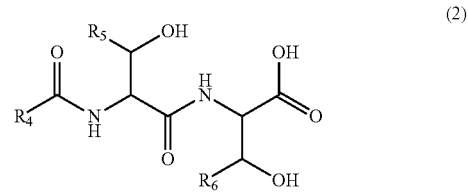

wherein $R_4$ is a saturated or unsaturated, linear or branched-chain hydrocarbon group having 7 to 25 carbon atoms, and $R_5$ and $R_6$ are each independently a hydrogen atom or an alkyl group having 1 to 6, preferably 1 to 5, carbon atoms.

$R_4$ is a saturated or unsaturated, linear or branched-chain hydrocarbon group having 7 to 25 carbon atoms. The carbon number is preferably 7 to 21, more preferably 7 to 15, further preferably 9 to 15, most preferably 9 to 13. The hydrocarbon group is preferably an alkyl group, specifically, an alkyl group having 7 to 25 carbon atoms, such as a heptyl group, an octyl group, a nonyl group, a decyl group, an undecyl group, a tridecyl group, a tetradecyl group, a pentadecyl group, a heptadecyl group, an octadecyl group, a nonadecyl group, an icosyl group, an eicosyl group, a henicosyl group, a heneicosyl group, a docosyl group, a tricosyl group, a tetracosyl group, a pentacosyl group, an isoheptyl group, an isooctyl group, an isononyl group, an isodecyl group, an isoundecyl group, an isotridecyl group, an isotetradecyl group, an isopentadecyl group, an isoheptadecyl group, an isooctadecyl group, an isononadecyl group, an isoicosyl group, an isoeicosyl group, an isohenicosyl group, an isoheneicosyl group, an isodocosyl group, an isotricosyl group, an isotetracosyl group, an isopentacosyl group and the like. From the aspect of high solubility, a group having 7 to 15 carbon atoms, such as a heptyl group, a nonyl group, an undecyl group, a tridecyl group, a pentadecyl group and the like, is preferable, a group having 9 to 13 carbon atoms, such as a nonyl group, an undecyl group, a tridecyl group and the like, are more preferable, and an undecyl group is most preferable.

$R_5$ and $R_6$ are each independently a hydrogen atom or an alkyl group having 1 to 6 carbon atoms. The alkyl group having 1 to 6 carbon atoms may be linear or branched-chain. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1,2-dimethylpropyl group, a 1-ethylpropyl group, a hexyl group, a isohexyl group, a 1,1-dimethylbutyl group, a 2,2-dimethylbutyl group, a 3,3-dimethylbutyl group, a 2-ethylbutyl group, and the like. Among these, an alkyl group having 1 to 5 carbon atoms is preferable, an alkyl group having carbon atoms 1 to 4 is more preferable, an alkyl group having carbon atoms 1 to 3 is further preferable, a methyl group, an ethyl group and a propyl group are particularly preferable, and a methyl group is most preferable. In the present invention, at least one of $R_5$ and $R_6$ is preferably a methyl group, and both of $R_5$ and $R_6$ are more preferably methyl groups.

Examples of compound (2) include 2-(2-decanoylamino-3-hydroxybutanoylamino)-3-hydroxybutanoic acid, 2-(2-decanoylamino-3-hydroxybutanoylamino)-3-hydroxypentanoic acid, 2-(2-decanoylamino-3-hydroxybutanoylamino)-3-hydroxyhexanoic acid, 2-(2-decanoylamino-3-hydroxybutanoylamino)-3-hydroxyheptanoic acid, 2-(2-decanoylamino-3-hydroxybutanoylamino)-3-hydroxyoctanoic acid, 2-(2-decanoylamino-3-hydroxypentenoylamino)-3-hydroxybutanoic acid, 2-(2-decanoylamino-3-hydroxyhexenoylamino)-3-hydroxybutanoic acid, 2-(2-decanoylamino-3-hydroxyheptenoylamino)-3-hydroxybutanoic acid, 2-(2-decanoylamino-3-hydroxyoctenoylamino)-3-hydroxybutanoic acid, 2-(2-dodecanoylamino-3-hydroxybutanoylamino)-3-hydroxybutanoic acid, 2-(2-dodecanoylamino-3-hydroxybutanoylamino)-3-hydroxypentanoic acid, 2-(2-dodecanoylamino-3-hydroxybutanoylamino)-3-hydroxyhexanoic acid, 2-(2-dodecanoylamino-3-hydroxybutanoylamino)-3-hydroxyheptanoic acid, 2-(2-dodecanoylamino-3-hydroxybutanoylamino)-3-hydroxyoctanoic acid, 2-(2-dodecanoylamino-3-hydroxypentenoylamino)-3-hydroxybutanoic acid, 2-(2-dodecanoylamino-3-hydroxyhexenoylamino)-3-hydroxybutanoic acid, 2-(2-dodecanoylamino-3-hydroxyheptenoylamino)-3-hydroxybutanoic acid, 2-(2-dodecanoylamino-3-hydroxyoctenoylamino)-3-hydroxybutanoic acid, 2-(2-tetradecanoylamino-3-hydroxybutanoylamino)-3-hydroxybutanoic acid, 2-(2-tetradecanoylamino-3-hydroxybutanoylamino)-3-hydroxypentanoic acid, 2-(2-tetradecanoylamino-3-hydroxybutanoylamino)-3-hydroxyhexanoic acid, 2-(2-tetradecanoylamino-3-hydroxybutanoylamino)-3-hydroxyheptanoic acid, 2-(2-tetradecanoylamino-3-hydroxybutanoylamino)-3-hydroxyoctanoic acid, 2-(2-tetradecanoylamino-3-hydroxypentenoylamino)-3-hydroxybutanoic acid, 2-(2-tetradecanoylamino-3-hydroxyhexenoylamino)-3-hydroxybutanoic acid, 2-(2-tetradecanoylamino-3-hydroxyheptenoylamino)-3-hydroxybutanoic acid, 2-(2-tetradecanoylamino-3-hydroxyoctenoylamino)-3-hydroxybutanoic acid and the like. Of these, 2-(2-decanoylamino-3-hydroxybutanoylamino)-3-hydroxybutanoic acid, 2-(2-dodecanoylamino-3-hydroxybutanoylamino)-3-hydroxybutanoic acid, and 2-(2-tetradecanoylamino-3-hydroxybutanoylamino)-3-hydroxybutanoic acid are preferable, and 2-(2-dodecanoylamino-3-hydroxybutanoylamino)-3-hydroxybutanoic acid is most preferable.

Component C in the present invention can be a salt of compound (2). While the salt of compound (2) is not particularly limited, for example, alkali metal salts such as sodium salt, potassium salt, lithium salt and the like; alkaline earth metal salts such as calcium salt, magnesium salt and the like; ammonium salts such as alkanol amine salt and the like; basic organic compound salt and the like can be mentioned. Since the solubility can be improved, sodium salt, potassium salt and ammonium salt are preferable, sodium salt and potassium salt are more preferable, and sodium salt is most preferable.

Component C in the present invention can be produced by a known method. For example, component C can be synthesized by condensing 2-alkanoylamino-3-hydroxyalkanoic acid and 2-amino-3-hydroxyalkanoic acid methyl ester with a condensing agent such as dicyclohexylcarbodiimide and the like, and hydrolyzing methyl ester with a base such as sodium hydroxide and the like. Examples of 2-alkanoylamino-3-hydroxyalkanoic acid include 2-decanoylamino-3-hydroxybutanoic acid, 2-decanoylamino-3-hydroxypentanoic acid, 2-decanoylamino-3-hydroxyhexanoic acid, 2-dodecanoylamino-3-hydroxybutanoic acid, 2-dodecanoylamino-3-hydroxypentanoic acid, 2-dodecanoylamino-3-hydroxyhexanoic acid, 2-tetradecanoylamino-3-hydroxybutanoic acid, 2-tetradecanoylamino-3-hydroxypentanoic acid, 2-tetradecanoylamino-3-hydroxyhexanoic acid and the like. Examples of 2-amino-3-hydroxyalkanoic acid methyl ester include 2-amino-3-hydroxybutanoic acid methyl ester, 2-amino-3-hydroxypentanoic acid methyl ester, 2-amino-3-hydroxyhexanoic acid methyl ester and the like.

The content of component C in the cleansing composition of the present invention is preferably not less than 0.0001 wt %, more preferably not less than 0.001 wt %, further preferably not less than 0.01 wt %, still more preferably not less than 0.03 wt %, of the cleansing composition. The content of component C is preferably not more than 50 wt %, more preferably not more than 45 wt %, further preferably not more than 40 wt %, still more preferably not more than 30 wt %, of the cleansing composition since the stability in dissolution state is superior.

The weight ratio of component C relative to the total weight of component A and component C (C/(A+C)) in the cleansing composition of the present invention is preferably not less than 0.01, more preferably not less than 0.1, further preferably not less than 0.2, still more preferably not less than 0.3, especially preferably not less than 0.4, particularly preferably not less than 0.5. The weight ratio of component C relative to the total weight of component A and component C (C/(A+C)) in the cleansing composition of the present invention is preferably not more than 0.999, more preferably not more than 0.99, further preferably not more than 0.97, still more preferably not more than 0.95, especially preferably not more than 0.93, particularly preferably not more than 0.91.

The cleansing composition of the present invention encompasses a cleansing composition containing component A, a cleansing composition containing component A and component B, cleansing composition containing component A and component C, and a cleansing composition containing component A, component B and component C.

The pH of the cleansing composition of the present invention is not particularly limited as long as it does not inhibit the effect of the present invention. The pH of the cleansing composition of the present invention is preferably not less than 4.0, more preferably not less than 4.5, further preferably not less than 5.0, still more preferably not less than 5.5, especially preferably not less than 6.0, particularly preferably not less than 6.5, from the aspects of appropriate amount and quality of lather, and stability in dissolution state. The pH of the cleansing composition of the present invention is preferably not more than 11.0, more preferably not more than 10.5, further preferably not more than 10.0, still more preferably not more than 9.5, especially preferably not more than 9.0, particularly preferably not more than 8.5, from the aspects of appropriate amount and quality of lather, and the stability in dissolution state.

The cleansing composition of the present invention can further contain as appropriate, besides the above-mentioned components, a component used for general cleansing compositions and the like according to the object, as long as the effect of the present invention is not inhibited. While such component is not particularly limited, for example, pH adjuster, vitamins, moisturizer, antimicrobial agent, anti-inflammatory agent, algefacient, preservative, pearly sheen agent, various chelating agents, various powders, flavor, dye, UV absorber, antioxidant and the like can be mentioned.

The cleansing composition of the present invention can be produced by using component A. To be specific, it can be produced by adding component A to other components constituting the cleansing composition and mixing them, or adding other components constituting the cleansing composition to component A and mixing them. The addition and mixing can be performed by a method known per se. The form of the cleansing composition of the present invention is not particularly limited, and can take any form such as solid, liquid (including slurry), gel, paste and the like. In addition, the appearance of the cleansing composition of the present invention is not particularly limited, and any appearance can be selected as appropriate such as transparent, white turbid, pearl-like and the like.

Various cosmetic agents can be prepared by adding the cleansing composition of the present invention. Specific examples include cleansing powder, cleansing foam, powder soap, solid soap, body shampoo, hair shampoo (powdery shampoo, liquid shampoo), oral cleaning agent such as toothpaste and the like, shaving foam, makeup removing agent, cleansing agent and the like.

The form of the cosmetic agent in the present invention is not particularly limited, and any form can be taken such as solid, liquid (including slurry), gel, paste and the like.

The cosmetic agent in the present invention can appropriately further contain, according to an object, various components generally used for cosmetic agents and the like, as long as the effect of the present invention is not inhibited. To be specific, a component such as oil, surfactant, thickener, preservative, flavor, UV absorber, moisturizer, physiological activity component, antioxidant, anti-inflammatory agent, antibacterial agent, adiaphoretic, chelating agent, neutralization agent, pH adjuster and the like can be added according to the specific use or agent form of the cosmetic agent.

EXAMPLES

The present invention is explained in more detail in the following by referring to Examples, which are not to be construed as limitative.

Synthetic Example 1

2-dodecanamido-2-butenoic acid

Lauryl amide (26.03 g), 2-ketobutanoic acid (20.00 g) and toluene (280 g) were mixed, and the mixture was heated under reflux for 14 hr. After cooling, the precipitate was collected by filtration to give a crude product. The product was recrystallized from toluene and dried to give 2-dodecanamido-2-butenoic acid (20.43 g).

$^1$H-NMR (400 MHz, CD3OD, r.t.): δ6.83 (1H, q, J=7.1 Hz), 2.35 (2H, t, J=7.3 Hz), 1.76 (3H, d, J=7.1 Hz), 1.68 (2H, m), 1.47-1.24 (16H, m), 0.92 (3H, t, J=6.7 Hz)

ESI-MS (positive) m/z 284 [M+H]+(negative) m/z 282 [M−H]−

Synthetic Example 2 sodium 2-dodecanamido-2-butenate

2-Dodecanamido-2-butenoic acid obtained in Synthetic Example 1 was dispersed in water, and 27 wt % aqueous sodium hydroxide solution was added dropwise. The mixture was neutralized and the concentration was adjusted with ion exchange water to give 10 wt % aqueous solution of sodium 2-dodecanamido-2-butenate.

Synthetic Example 3

2-tetradecanamido-2-butenoic acid

In the same manner as in Synthetic Example 1 except that myristyl amide (29.69 g) was used instead of lauryl amide, 2-tetradecanamido-2-butenoic acid was obtained.

Synthetic Example 4 sodium 2-tetradecanamido-2-butenate

In the same manner as in Synthetic Example 2 except that sodium 2-tetradecanamido-2-butenate obtained in Synthetic Example 3 was used instead of 2-dodecanamido-2-butenoic acid, sodium 2-tetradecanamido-2-butenate was obtained.

Synthetic Example 5

2-decanamido-2-hexenoic acid

In the same manner as in Synthetic Example 1 except that 2-ketohexanoic acid (25.49 g) was used instead of 2-ketobutanoic acid, 2-decanamido-2-hexenoic acid was obtained.

Synthetic Example 6 sodium 2-decanamido-2-hexenate

In the same manner as in Synthetic Example 2 except that 2-decanamido-2-hexenoic acid obtained in Synthetic Example 5 was used instead of 2-dodecanamido-2-butenoic acid, sodium 2-decanamido-2-hexenate was obtained.

Synthetic Example 7

2-(2-dodecanoylamino-3-hydroxybutanoylamino)-3-hydroxybutanoic acid

2-Dodecanoylamino-3-hydroxybutanoic acid (15.07 g) and 2-amino-3-hydroxybutanoic acid methyl ester (6.66 g) were condensed with dicyclohexylcarbodiimide (10.31 g). Thereafter, methyl ester was hydrolyzed with sodium hydroxide to give 2-(2-dodecanoylamino-3-hydroxybutanoylamino)-3-hydroxybutanoic acid (10.24 g). The structure thereof was identified by $^1$H-NMR (400 MHz, CD3OD, r.t.).

Experimental Example 1

Evaluation of Amount and Quality of Lather Provided by Component A

Sodium 2-dodecanamido-2-butenate, sodium 2-tetradecanamido-2-butenate and sodium 2-decanamido-2-hexenate synthesized in the above-mentioned Synthetic Examples 2, 4 and 6 were respectively dissolved in ion exchange water to 0.1 wt %, and the cleansing compositions of Examples 1-5 shown in the following Table 1 were prepared. Various cleansing compositions were adjusted to pH 6-9 with sodium hydroxide.

<Evaluation Method>

(1) Amount of Lather

Various cleansing compositions (50 g) were stirred by Millser (IFM-150, manufactured by Iwatani Corporation), in a graduated cylindrical container (inner diameter 70 mm, height 135 mm) at 30° C. for 5 seconds and, 1 minute after completion of stirring, the volume of lather in the container was measured. The measured volume of lather was taken as the amount of lather and evaluated according to the following criteria.

not less than 230 mL: ⊙
not less than 170 mL and less than 230 mL: ○
not less than 120 mL and less than 170 mL: Δ
less than 120 mL: x (2) Quality of Lather Each cleansing composition (1.0 mL) was taken and lather was made on the palm for 5 min. The quality of lather was evaluated on average by 10 professional panelists according to the following criteria.

dense lather quality, elastic: ⊙
rather dense lather quality, rather elastic: ○
rather rough lather quality: Δ
rough lather quality: x (3) pH Measurement Using a pH meter (Horiba, Ltd. (F-52)) calibrated with a predetermined buffered solution (pH 9.18, pH 6.86, pH 4.01), the pH of the cleansing composition (50 mL) was measured.

TABLE 1

| component (wt %) | | Example 1 | Example 2 | Example 3 | Example 4 | Example 5 | Comp. Ex. 1 |
|---|---|---|---|---|---|---|---|
| Component A | sodium 2-tetradecanamido-2-butenate | — | — | — | 0.1 | — | — |
| | sodium 2-decanamido-2-hexenate | — | — | — | — | 0.1 | — |
| | sodium 2-dodecanamido-2-butenate | 0.1 | 0.1 | 0.1 | — | — | — |
| Component B | sodium laurate | — | — | — | — | — | 0.1 |
| ion exchange water | | rest | rest | rest | rest | rest | rest |
| total | | 100 | 100 | 100 | 100 | 100 | 100 |
| pH (adjusted with NaOH) | | 6.0 | 8.0 | 9.0 | 6.0 | 6.0 | 8.0 |
| lather amount (mL) | | 190 | 215 | 220 | 190 | 170 | 120 |
| lather amount evaluation | | ○ | ○ | ○ | ○ | ○ | Δ |
| lather quality evaluation | | ○ | ○ | ○ | ○ | ○ | Δ |

The results shown in Table 1 have clarified that the amount of lather is not less than 170 mL in all Examples, and component A provides a sufficient amount of lather to the cleansing composition. From the aspect of the lather amount, sodium 2-dodecanamido-2-butenate and sodium 2-tetradecanamido-2-butenate of component A were found to be superior to sodium 2-decaneamido-2-hexadeceneate. In addition, the lather quality was evaluated as "○" in all Examples, and use of component A was clarified to improve the lather quality of the cleansing composition.

Experimental Example 2

Effect of Component A and Component B

Using sodium 2-dodecanamido-2-butenate, which was synthesized in the above-mentioned Synthetic Example 2, as component A and sodium laurate as component B, the amount and quality of lather when the both are contained in the cleansing composition were evaluated. To be specific, the cleansing compositions of Examples 6-9 and Comparative Example 2 having the compositions shown in Table 2 below were prepared, pH was adjusted to 8 with sodium hydroxide, and the amount of lather was measured according to the method shown in the above-mentioned Experimental Example 1.

TABLE 2

| component (wt %) | | Example 6 | Example 7 | Example 8 | Example 9 | Comp. Ex. 2 |
|---|---|---|---|---|---|---|
| Component A | sodium 2-dodecanamido-2-butenate | 0.10 | 0.08 | 0.06 | 0.04 | — |
| Component B | sodium laurate | — | 0.02 | 0.04 | 0.06 | 0.10 |
| water | | rest | rest | rest | rest | rest |
| total | | 100 | 100 | 100 | 100 | 100 |
| pH (adjusted with NaOH) | | 8.0 | 8.0 | 8.0 | 8.0 | 8.0 |
| lather amount (mL) | | 215 | 230 | 235 | 230 | 120 |
| lather amount evaluation | | ○ | ⊙ | ⊙ | ⊙ | Δ |
| lather quality | | ○ | ⊙ | ⊙ | ⊙ | Δ |

As is clear from the results shown in Table 2, when sodium 2-dodecanamido-2-butenate and sodium laurate were combined in the cleansing composition, the measured amount of the lather increased markedly, and the quality of the lather was also improved. Hence, it has been clarified that the combination of the both (i.e., component A and component B) affords a synergistic effect on the increase in the lather amount and improvement of the lather quality of the cleansing composition.

Formulation Example 1

A cleansing composition having the composition shown in Table 3 below was prepared.

TABLE 3

| component | amount added (wt %) |
|---|---|
| Sodium 2-dodecaneamido-2-buteneate (Component A) | 5 |
| 2-(2-dodecanoylamino-3-hydroxybutanoylamino)-3-hydroxybutanoic acid Na (Component C) | 6 |
| water | rest | pH 7.0

Formulation Example 2

A cleansing composition having the composition shown in Table 4 below was prepared.

TABLE 4

| component | amount added (wt %) |
|---|---|
| Sodium 2-dodecaneamido-2-buteneate (Component A) | 3 |
| Sodium myristate (Component B) | 2 |
| 2-(2-dodecanoylamino-3-hydroxybutanoylamino)-3-hydroxybutanoic acid Na (Component C) | 3 |
| water | rest | pH 8.0

Formulation Example 3

A shampoo having the composition shown in Table 5 below was prepared.

TABLE 5

| component | amount added (wt %) |
|---|---|
| Polyquaternium-10 *1 | 0.2 |
| lauryl sulfosuccinate 2Na *2 | 10.8 |
| cocamidopropyl betaine *3 | 3 |
| Sodium 2-dodecanamido-2-buteneate | 1 |
| PEG-7 glyceryl cocoate *4 | 2 |
| Sodium PCA *5 | 1 |
| sodium chloride | 0.8 |
| EDTA | 0.1 |
| preservative | q.s. |
| citric acid | q.s. |
| flavor | q.s. |
| water | rest |

*1 polymer JR-400 (IWASE COSFA CO., LTD.)
*2 Kohacool L-40 (TOHO Chemical Industry Co., Ltd.)
*3 Amphitol 55AB (Kao Corporation)
*4 Cetiol HE (Cognis Japan Ltd.)
*5 AJIDEW NL-50 (Ajinomoto Co., Inc.)
pH 6.0

Formulation Example 4

A shampoo having the composition shown in Table 6 below was prepared.

TABLE 6

| component | amount added (wt %) |
|---|---|
| Lauroamphoacetate Na *1 | 30 |
| Lauryl sulfoacetate Na *2 | 15 |
| Sodium 2-dodecaneamido-2-butenate | 0.5 |
| glycerol | 3.6 |
| Sodium PCA *3 | 0.5 |
| citric acid | q.s. |
| flavor | q.s. |
| water | rest |

*1 MIRANOL ULTRA L-32E (Rhodia)
*2 NIKKOL LSA-F (Nikko Chemicals Co., Ltd.)
*3 AJIDEW NL-50 (Ajinomoto Co., Inc.)
pH 5.6

Formulation Example 5

A body shampoo having the composition shown in Table 7 below was prepared.

TABLE 7

| component | amount added (wt %) |
|---|---|
| Sodium 2-dodecanamido-2-butenate | 6 |
| 2-(2-dodecanoylamino-3-hydroxybutanoylamino)-3-hydroxybutanoic acid Na | 7 |
| glyceryl laurate *1 | 2 |
| lauramidopropyl hydroxysultaine (29%) *2 | 9 |
| Amodimethicone *3 | 0.4 |
| glycerol | 1.5 |
| Sodium PCA *4 | 0.8 |
| citric acid | q.s. |
| flavor | q.s. |
| water | rest |

*1 SUNSOFT No. 750 (Taiyo Kagaku Co., Ltd.)
*2 Softazoline LSB (Kawaken Fine Chemicals Co., Ltd.)
*3 FZ-4671 (Dow Corning Toray Co., Ltd.)
*4 AJIDEW NL-50 (Ajinomoto Co., Inc.)
pH 6.0

Formulation Example 6

A body shampoo having the composition shown in Table 8 below was prepared.

TABLE 8

| component | amount added (wt %) |
|---|---|
| Sodium 2-dodecanamido-2-butenate | 3 |
| myristic acid Na | 9 |
| 2-(2-dodecanoylamino-3-hydroxybutanoylamino)-3-hydroxybutanoic acid Na | 4 |
| lactic acid Na | 1.8 |
| hydroxide Na | 0.2 |
| citric acid | q.s. |
| flavor | q.s. |
| water | rest | pH 7.8

The cleansing composition of Formulation Example 1 was a cleansing composition having good amount and good quality of lather. The cleansing composition of Formulation Example 2 was a cleansing composition affording slippery touch (smooth touch) after washing, hair slippery touch (dry touch), hair lightness and hair combing property, and showing less slimy touch and sliminess. In addition, all compositions of Formulation Examples 1-6 were superior in the amount and quality of lather as well as stable in quality. That is, the compositions were free of coloration and odorization, and did not show any change in the viscosity, precipitation or pH change. Furthermore, they were satisfactory compositions even when used for rough skin and damaged hair.

INDUSTRIAL APPLICABILITY

Using a particular alkenoic acid or a salt thereof, a cleansing composition providing good amount and good quality of lather can be provided. Hence, the cleansing composition of the present invention is useful for increasing the amount of lather and improving the quality of lather. In addition, the cleansing composition is stable in various formulations, and also useful for rough skin and damaged hair.

This application is based on a patent application No. 2011-102500 (filing date: Apr. 28, 2011) filed in Japan, the contents of which are incorporated in full herein.

The invention claimed is:

1. A cleansing composition, comprising:
at least one compound represented by formula (1):

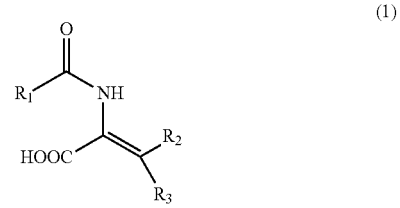

(1)

where $R_1$ is a saturated or unsaturated, linear or branched-chain hydrocarbon group having 11 to 25 carbon atoms, and $R_2$ and $R_3$ are each independently a hydrogen atom or an alkyl group having 1 to 6 carbon atoms, or a salt thereof and wherein the cleansing composition is formulated as a cosmetic agent.

2. A cleansing composition according to claim 1, wherein $R_2$ and $R_3$ are each independently a hydrogen atom or an alkyl group having 1 to 5 carbon atoms.

3. A cleansing composition according to claim 1, wherein $R_1$ is a saturated or unsaturated, linear or branched-chain hydrocarbon group having 11 to 13 carbon atoms.

4. A cleansing composition according to claim 2, wherein $R_1$ is a saturated or unsaturated, linear or branched-chain hydrocarbon group having 11 to 13 carbon atoms.

5. A cleansing composition according to claim 1, wherein one of $R_2$ and $R_3$ is a methyl group, and the other is a hydrogen atom.

6. A cleansing composition according to claim 2, wherein one of $R_2$ and $R_3$ is a methyl group, and the other is a hydrogen atom.

7. A cleansing composition according to claim 3, wherein one of $R_2$ and $R_3$ is a methyl group, and the other is a hydrogen atom.

8. A cleansing composition according to claim 1, wherein said at least one compound represented by formula (1) is 2-dodecanamido-2-butenoic acid or a salt thereof.

9. A cleansing composition according to claim 1, further comprising:
at least one fatty acid or a salt thereof.

10. A cleansing composition according to claim 9, wherein said at least one fatty acid or salt thereof is lauric acid or a salt thereof.

11. A cleansing composition according to claim 1, further comprising:
at least one compound represented by formula (2):

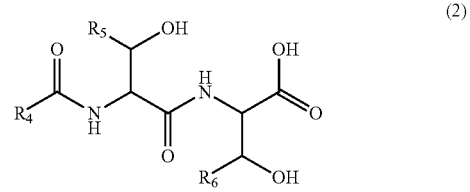

(2)

wherein $R_4$ is a saturated or unsaturated, linear or branched-chain hydrocarbon group having 7 to 25 carbon atoms, and $R_5$ and $R_6$ are each independently a hydrogen atom or an alkyl group having 1 to 6 carbon atoms, or a salt thereof.

12. A cleansing composition according to claim 11, wherein $R_5$ and $R_6$ are each independently a hydrogen atom or an alkyl group having 1 to 5 carbon atoms.

13. A cleansing composition according to claim 11, wherein $R_4$ is a saturated or unsaturated, linear or branched-chain hydrocarbon group having 9 to 13 carbon atoms.

14. A cleansing composition according to claim 12, wherein $R_4$ is a saturated or unsaturated, linear or branched-chain hydrocarbon group having 9 to 13 carbon atoms.

15. A cleansing composition according to claim 11, wherein $R_5$ and $R_6$ are each a methyl group.

16. A cleansing composition according to claim 11, wherein said at least one compound represented by formula (2) is 2-(2-dodecanoylamino-3-hydroxybutanoylamino)-3-hydroxybutanoic acid or a salt thereof.

17. A method of improving the lather of a cleansing composition, comprising adding at least one compound represented by formula (1):

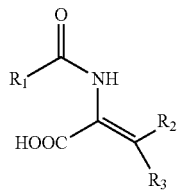
(1)

wherein $R_1$ is a saturated or unsaturated, linear or branched-chain hydrocarbon group having 11 to 25 carbon atoms, and $R_2$ and $R_3$ are each independently a hydrogen atom or an alkyl group having 1 to 6 carbon atoms, or a salt thereof, and at least one ingredient selected from the group consisting of an anti-inflammatory agent, an algefacient, a pearly sheen agent, and an UV absorber, to a cleansing composition.

18. A method for cleansing skin or hair, comprising contacting skin or hair with a cleansing composition according to claim 1.

19. A cleansing composition according to claim 1, further comprising at least one ingredient selected from the group consisting of a pH adjuster, a vitamin, a moisturizer, an antimicrobial agent, an anti-inflammatory agent, an algefacient, a preservative, a pearly sheen agent, a chelating agent, a flavor, a dye, an UV absorber, and an antioxidant.

* * * * *